US012782318B2

(12) United States Patent
Hirosue et al.

(10) Patent No.: US 12,782,318 B2
(45) Date of Patent: Nov. 3, 2026

(54) OIL AND FAT DETERIORATION PREDICTION DEVICE, DETERIORATION PREDICTION SYSTEM, DETERIORATION PREDICTION METHOD, OIL AND FAT REPLACEMENT SYSTEM, AND FRYER SYSTEM

(71) Applicant: J-OIL MILLS, Inc., Tokyo (JP)

(72) Inventors: Yoriyasu Hirosue, Tokyo (JP); Takashi Yamaguchi, Tokyo (JP); Masaharu Hashimoto, Tokyo (JP); Shinsuke Kozono, Tokyo (JP)

(73) Assignee: J-OIL MILLS, Inc., Tokyo (JP)

( * ) Notice: Subject to any disclaimer, the term of this patent is extended or adjusted under 35 U.S.C. 154(b) by 509 days.

(21) Appl. No.: 17/767,691

(22) PCT Filed: Sep. 28, 2020

(86) PCT No.: PCT/JP2020/036682
§ 371 (c)(1),
(2) Date: Apr. 8, 2022

(87) PCT Pub. No.: WO2021/079692
PCT Pub. Date: Apr. 29, 2021

(65) Prior Publication Data

US 2024/0019400 A1 Jan. 18, 2024

(30) Foreign Application Priority Data

Oct. 24, 2019 (JP) ................................ 2019-193843

(51) Int. Cl.
*G01N 33/03* (2006.01)
*A47J 37/12* (2006.01)
*G01N 29/036* (2006.01)

(52) U.S. Cl.
CPC ........ *G01N 29/036* (2013.01); *A47J 37/1266* (2013.01); *G01N 33/03* (2013.01); *G01N 2291/0226* (2013.01)

(58) Field of Classification Search
CPC ............................ G01N 33/03; G01N 29/036
See application file for complete search history.

(56) References Cited

U.S. PATENT DOCUMENTS 5,586,486 A 12/1996 Nitschke et al.
5,767,407 A * 6/1998 Sinha .................... G01N 29/52 73/61.79

(Continued)

FOREIGN PATENT DOCUMENTS

JP 6-178731 A 6/1994
JP 7-99887 A 4/1995

(Continued)

OTHER PUBLICATIONS

PCT International Preliminary Report on Patentability and Written Opinion of the International Searching Authority dated Dec. 8, 2020 filed in PCT/JP2020/036682; English translation.

(Continued)

*Primary Examiner* — Suman K Nath
*Assistant Examiner* — Alex T Devito
(74) *Attorney, Agent, or Firm* — RANKIN, HILL & CLARK LLP

(57) ABSTRACT

To provide a deterioration prediction device with which it is possible to easily and precisely predict deterioration of an edible oil and fat.
The deterioration prediction device 1 of the present invention comprises an acoustic data acquisition unit 2 that acquires acoustic data from when a fried food article is cooked using a fry oil, an indicator extraction unit 11 within a processing unit 3 (control unit 10) that extracts an indicator (Continued)

pertaining to deterioration of the fry oil from the acquired acoustic data, and a comparative assessment unit 13 that assesses the extent of deterioration of an oil and fat, based on the indicator extracted by the indicator extraction unit 11.

7 Claims, 12 Drawing Sheets

(56) References Cited

U.S. PATENT DOCUMENTS

| | | | | |
|---|---|---|---|---|
| 10,859,553 | B2 | 12/2020 | Yamasaki et al. | |
| 2010/0260903 | A1* | 10/2010 | Wei | G01N 21/645 250/459.1 |
| 2017/0184551 | A1* | 6/2017 | Bai | G01N 33/14 |
| 2017/0219546 | A1* | 8/2017 | Yamasaki | G01N 29/022 |
| 2017/0219547 | A1 | 8/2017 | Yamasaki | |

FOREIGN PATENT DOCUMENTS

| | | | |
|---|---|---|---|
| JP | H0799887 | * | 4/1995 |
| JP | H11118774 | * | 4/1999 |
| JP | 2003-83951 A | | 3/2003 |
| JP | 6448811 B2 | | 1/2019 |

OTHER PUBLICATIONS

International Search Report (ISR) dated Dec. 8, 2020 filed in PCT/JP2020/036682.

"What is the standard time for replacing cooking (frying) oil?", goo, NTT Resonant Incorporated, Best answer column, 2005, from Internet <URL:https://oshiete.goo.ne.jp/qa/1424984.html>; English translation.

Taiwanese Office Action/Search Report dated Nov. 27, 2023 issued in Taiwanese patent application No. 109135513 and its English machine translation.

Japanese Office Action (JPOA) mailed on Aug. 8, 2024 issued in Japanese patent application No. 2021-554201 and its English machine translation.

"The benefits of clarifying when to change fryer oil", Bottleneck Solutions, 2016, Retrieved Jul. 30, 2024, from Internet <URL:https://karattokun.bn-solutions.jp/oil/av-checking/> and its English machine translation.

"Changing the tempura oil", Edo soba hand-made restaurant Nagareyama Shozan, Nov. 24, 2016, Retrieved Jul. 30, 2024, from Internet <URL:https://shouzan.jp/archives/667> and its English machine translation.

* cited by examiner

HEATING TIME: PREDICTED (PREDICTED VALUE) VS. ACTUAL (ACTUAL MEASURED VALUE)

| HEATING TIME | MEAN MEASURED VALUE | STANDARD DEVIATION |
|---|---|---|
| 8h | 8.9h | 1.4 |
| 16h | 18.1h | 0.9 |
| 24h | 20.2h | 0.6 |
| 32h | 32.8h | 1.8 |

ACID VALUE: PREDICTED (PREDICTED VALUE) VS. ACTUAL (ACTUAL MEASURED VALUE)

· ACID VALUE

| HEATING TIME | ACTUAL MEASURED VALUE | MEAN PREDICTED VALUE | STANDARD DEVIATION |
|---|---|---|---|
| 8h | 0.16 | 0.11 | 0.10 |
| 16h | 0.47 | 0.53 | 0.06 |
| 24h | 1.01 | 1.05 | 0.07 |
| 32h | 1.75 | 1.70 | 0.09 |

HEATING TIME: PREDICTED (PREDICTED VALUE) VS. ACTUAL (ACTUAL MEASURED VALUE)

| HEATING TIME | MEAN PREDICTED VALUE | STANDARD DEVIATION |
|---|---|---|
| 8h | 9.0h | 1.8 |
| 16h | 15.6h | 1.1 |
| 24h | 23.0h | 1.2 |
| 32h | 32.4h | 1.6 |

ACID VALUE: PREDICTED (PREDICTED VALUE) VS. ACTUAL (ACTUAL MEASURED VALUE)

· ACID VALUE

| HEATING TIME | ACTUAL MEASURED VALUE | MEAN PREDICTED VALUE | STANDARD DEVIATION |
|---|---|---|---|
| 8h | 0.16 | 0.13 | 0.12 |
| 16h | 0.47 | 0.54 | 0.07 |
| 24h | 1.01 | 1.00 | 0.10 |
| 32h | 1.75 | 1.71 | 0.13 |

COLOR (Y+10R): PREDICTED (PREDICTED VALUE) VS. ACTUAL (ACTUAL MEASURED VALUE)

· COLOR (Y+10R)

| HEATING TIME | ACTUAL MEASURED VALUE | MEAN PREDICTED VALUE | STANDARD DEVIATION |
|---|---|---|---|
| 8h | 6.5 | 6.9 | 1.6 |
| 16h | 10.7 | 11.0 | 0.9 |
| 24h | 18.0 | 17.3 | 1.2 |
| 32h | 24.0 | 24.1 | 1.3 |

RATE OF INCREASE IN VISCOSITY: PREDICTED (PREDICTED VALUE) VS. ACTUAL (ACTUAL MEASURED VALUE)

· RATE OF INCREASE IN VISCOSITY

| HEATING TIME | ACTUAL MEASURED VALUE | MEAN PREDICTED VALUE | STANDARD DEVIATION |
|---|---|---|---|
| 8h | 3.52 | 3.87 | 0.57 |
| 16h | 6.16 | 5.98 | 0.33 |
| 24h | 8.62 | 8.29 | 0.37 |
| 32h | 11.02 | 11.18 | 0.50 |

OIL AND FAT DETERIORATION PREDICTION DEVICE, DETERIORATION PREDICTION SYSTEM, DETERIORATION PREDICTION METHOD, OIL AND FAT REPLACEMENT SYSTEM, AND FRYER SYSTEM

TECHNICAL FIELD

The present invention relates to a deterioration prediction device that predicts the extent of deterioration of an oil and fat, a deterioration prediction system, a deterioration prediction method, an oil and fat replacement system, and a fryer system.

BACKGROUND ART

Edible oils and fats used when cooking fried food articles deteriorate as numerous foods are cooked over time, and therefore must be replaced in appropriate periods. Devices are known that detect and assess the color tone, viscosity, odor, etc., of the oil and fat in order to objectively judge these oil and fat replacement periods.

For example, in the sensing device of Patent Document 1, a sensor unit is attached to a ventilation fan above an oil vat. The sensor unit has a sensitive film to which gas molecules serving as a source of an odor adsorb, and a transducer that converts the gas molecules adhering to the sensitive film into electrical signals, the sensor unit detecting an odor generated from an edible oil. A control unit of the sensing device assesses the extent of deterioration of the edible oil, based on information relating to the odor detected by the sensor unit during frying, and the type of food product being cooked using the edible oil (paragraphs [0017] and [0021], and FIG. 1).

RELATED ART DOCUMENTS

Patent Documents

[Patent Document 1] Japanese Patent No. 6448811

DISCLOSURE OF THE INVENTION

Problems the Invention is Intended to Solve

However, in the case of the sensing device of Patent Document 1, a variety of odors other than that of the food being cooked (fragrant odors, burnt odors, etc., emanating from articles other than fried food articles) are present within a kitchen, and it is therefore difficult to precisely predict deterioration of the edible oil from odor alone.

In view of such matters, it is accordingly an object of the present invention to provide a deterioration prediction device with which it is possible to easily and precisely predict deterioration of an oil and fat.

Means for Solving the Problems

A deterioration prediction device of the present invention is the device that predicts the extent of deterioration of an edible oil and fat, the deterioration prediction device comprising: an acoustic data acquisition unit that acquires acoustic data from when a fried food article is cooked using the oil and fat, which is accommodated in an oil vat; an indicator extraction unit that extracts an indicator pertaining to deterioration of the oil and fat from the acoustic data acquired by the acoustic data acquisition unit; and an assessment unit that assesses the extent of deterioration of the oil and fat, based on the indicator extracted by the indicator extraction unit.

The acoustic data acquisition unit of the deterioration prediction device acquires acoustic data of the oil and fat from when a fried food article such as tempura is cooked. The indicator extraction unit extracts various acoustic components, such as the frequency mean and the frequency standard deviation, from the acoustic data as indicators pertaining to deterioration of the oil and fat. The assessment unit assesses the extent of deterioration of the oil and fat, i.e., whether deterioration has advanced due to use, based on the indicators. Thus, this device can easily and precisely predict deterioration of the oil and fat.

In the deterioration prediction device of the present invention, it is preferred that the device furthermore comprises a notification unit that issues a notification regarding the extent of deterioration of the oil and fat or regarding a replacement timing for the oil and fat, the notification unit issuing the notification when it is assessed by the assessment unit, based on the extent of deterioration of the oil and fat, that a predetermined replacement threshold value has been exceeded.

According to this configuration, because the notification unit of the deterioration prediction device issues a notification regarding the extent of deterioration of the oil and fat, a user can ascertain the usage state of the oil and fat. In addition, because the notification unit issues a notification regarding a replacement timing for the oil and fat from a predetermined threshold value, based on the result of assessment by the assessment unit, a user can replace the oil and fat at a suitable timing. The “replacement timing” may be a timing at which the fry oil is to be actually replaced, or may be a remaining time in which the oil and fat can be used as estimated from the current extent of deterioration of the oil and fat.

In the deterioration prediction device of the present invention, the indicator is preferably one or more selected from the frequency mean, the frequency standard deviation, the frequency median value, the frequency standard error, the frequency mode value, the frequency first quartile, the frequency third quartile, the frequency interquartile range, the frequency centroid, the frequency skewness, the frequency kurtosis, the frequency spectrum flat module, the frequency spectrum entropy, the frequency spectrum precision, the acoustic complexity index, the acoustic entropy, and the predominant frequency.

According to this configuration, one or a plurality of indicators having a strong correlation with deterioration of the oil and fat are selected as the indicator. Thus, this device can precisely predict the deterioration.

A deterioration prediction system of the present invention is the system that is formed from a detection device and a machine learning device, and predicts the extent of deterioration of an edible oil and fat, the deterioration prediction system being such that: the detection device is provided with an acoustic data acquisition unit for acquiring acoustic data from when a fried food article is cooked using the oil and fat, which is accommodated in an oil vat, a storage unit for storing a trained model that is created by the machine learning device and that can assess the deterioration of the oil and fat, and an assessment unit for assessing the extent of deterioration of the oil and fat from the acoustic data using the trained model; and the machine learning device is provided with a trained model creation unit for extracting an indicator pertaining to deterioration of the oil and fat from the acoustic data acquired by the acoustic data acquisition unit, carrying out machine learning through linear regression using the indicator, and creating the trained model.

The deterioration prediction system of the present invention is configured from the detection device and the machine learning device. In the detection device, the acoustic data acquisition unit acquires acoustic data of the oil and fat from when a fried food article is cooked, and the assessment unit assesses the extent of deterioration of the oil and fat using the trained model.

The trained model creation unit extracts the indicator pertaining to deterioration of the oil and fat from the acquired acoustic data, and carries out machine learning through linear regression. Thus, the trained model is updated, and therefore this system can easily and precisely predict deterioration of the oil and fat.

In the deterioration prediction system of the present invention, the linear regression is preferably one or more selected from single regression, multiple regression, partial least squares (PLS) regression, and orthogonal partial least squares (OPLS) regression.

Linear regression such as single regression, multiple regression, partial least squares (PLS) regression, or orthogonal partial least squares (OPLS) regression is used in creation of the trained model. Thus, this system can create a trained model that is capable of precisely assessing deterioration of the oil and fat.

In the deterioration prediction system of the present invention, it is preferable that the detection device and the machine learning device are integrally formed.

For example, installing the integrated deterioration prediction system of the present invention near an oil vat within a shop or a factory makes it possible for a user to acquire prediction results pertaining to the deterioration of the oil and fat on site.

In the deterioration prediction system of the present invention, it is preferable that the detection device is installed near the oil vat in the shop or factory, and the machine learning device is installed at a remote location set apart from the shop or factory.

The detection device having the acoustic data acquisition unit, etc., is installed near the oil vat of the shop or factory, but the machine learning device may be installed at a remote location from the shop. Because the machine learning device is separate from the detection device, the trained model created by the machine learning device can be acquired through telecommunication, etc.

In the deterioration prediction system of the present invention, it is preferable that the detection device is provided with a first communication unit that transmits the acoustic data acquired by the acoustic data acquisition unit to the machine learning device, and the machine learning device is provided with a second communication unit that receives the acoustic data from the detection device.

Because the detection device is provided with the first communication unit, the acoustic data is transmitted to the machine learning device. In addition, because the machine learning device is provided with the second communication unit, the acoustic data is received and machine learning is carried out. In case where the detection device and the machine learning device are separate devices, this system can transmit and receive data between the communication units and assign required operations.

In the deterioration prediction system of the present invention, the first communication unit and the second communication unit are preferably capable of communicating wirelessly.

Because the detection device can transmit the acoustic data to the machine learning device through wireless communication by the first communication unit, the function of the detection device can be minimized and the detection device can be reduced in size.

A deterioration prediction method of the present invention is the method that involves predicting the extent of deterioration of an edible oil and fat, the method comprising: an acoustic data acquisition step for acquiring acoustic data from when a fried food article is cooked using the oil and fat; an indicator extraction step for extracting an indicator pertaining to deterioration of the oil and fat from the acoustic data acquired in the acoustic data acquisition step; and an assessment step for assessing the extent of deterioration of the oil and fat, based on the indicator extracted in the indicator extraction step.

In the deterioration prediction method of the present invention, acoustic data of the oil and fat from when a fried food article such as tempura is cooked is acquired in the acoustic data acquisition step. Various acoustic components, such as the frequency mean and the frequency standard deviation, are extracted from the acoustic data as indicators pertaining to deterioration of the oil and fat in the indicator extraction step. An assessment as to the extent of deterioration of the oil and fat, i.e., as to whether deterioration has advanced due to use, is made, based on the indicators in the assessment step. Thus, in this method, it is possible to easily and precisely predict deterioration of the oil and fat.

An oil and fat replacement system of the present invention is such that, based on notification information relating to the extent of deterioration of the oil and fat as outputted from the deterioration prediction device described above, one or more operations are performed, the operations being selected from among: a) alerting an oil and fat vendor and ordering new oil and fat; b) alerting an oil and fat manufacturer and producing a plan for manufacturing or selling the oil and fat; c) alerting a general headquarters of shops or factories, or alerting an oil and fat manufacturer, and issuing a proposal or an instruction regarding the method of use of the oil and fat to the shops or factories being supervised; d) alerting a waste oil collector or an oil and fat manufacturer and making preparations to collect waste oil; and e) alerting a cleaning work provider and making preparations to clean the oil vat.

In the oil and fat replacement system of the present invention, based on notification information relating to the extent of deterioration of the oil and fat, the oil and fat vendor is alerted and new oil and fat is ordered when, e.g., the notification information is issued a prescribed number of times. In addition, based on the notification information, the oil and fat manufacturer is alerted and a plan for manufacturing or selling the oil and fat is produced. Thus, this system can establish a manufacturing or sales plan that corresponds to the pace of replacement of the oil and fat.

In the oil and fat replacement system, based on the notification information, the general headquarters for the shops or factories, or the oil and fat manufacturer, is alerted, and a proposal or instruction regarding the method of use of the oil and fat is issued to the shops or factories being supervised. For example, the general headquarters instructs the shops to use the oil and fat while replacing the oil and fat as appropriate without being wasteful. Furthermore, based on the notification information, the waste oil collector is alerted and preparations are made to collect the waste oil, and moreover, a cleaning work provider is alerted and preparations are made to clean the oil vat. Therefore, this system can promptly carry out operations from supply of fry oil to collection of waste oil.

A fryer system of the present invention comprises a valve control unit that, based on notification information relating to the extent of deterioration of the oil and fat as outputted from the deterioration prediction device described above, controls valves provided to the oil vat, the valve control unit automatically discharging the oil and fat accommodated in the oil vat as waste oil.

In the fryer system of the present invention, the valve control unit controls the valves of the oil vat, based on notification information relating to the extent of deterioration of the oil and fat. Thus, this system can automatically discharge the oil and fat during use as waste oil.

In the fryer system of the present invention, it is preferable that the valve control unit automatically supplies new oil to the oil vat.

According to this configuration, the valve control unit controls the valves in order to automatically supply new oil to the oil vat. Thus, this system makes it possible to reduce a series of workloads through which a user confirms the extent of deterioration of the oil and fat, discharges waste oil, and supplies new oil.

Effect of the Invention

According to the present invention, it is possible to easily and precisely predict deterioration of an oil and fat.

MODE FOR CARRYING OUT THE INVENTION

Embodiments of the deterioration prediction device according to the present invention are described below with reference to the accompanying drawings.

First Embodiment

Figure 1:
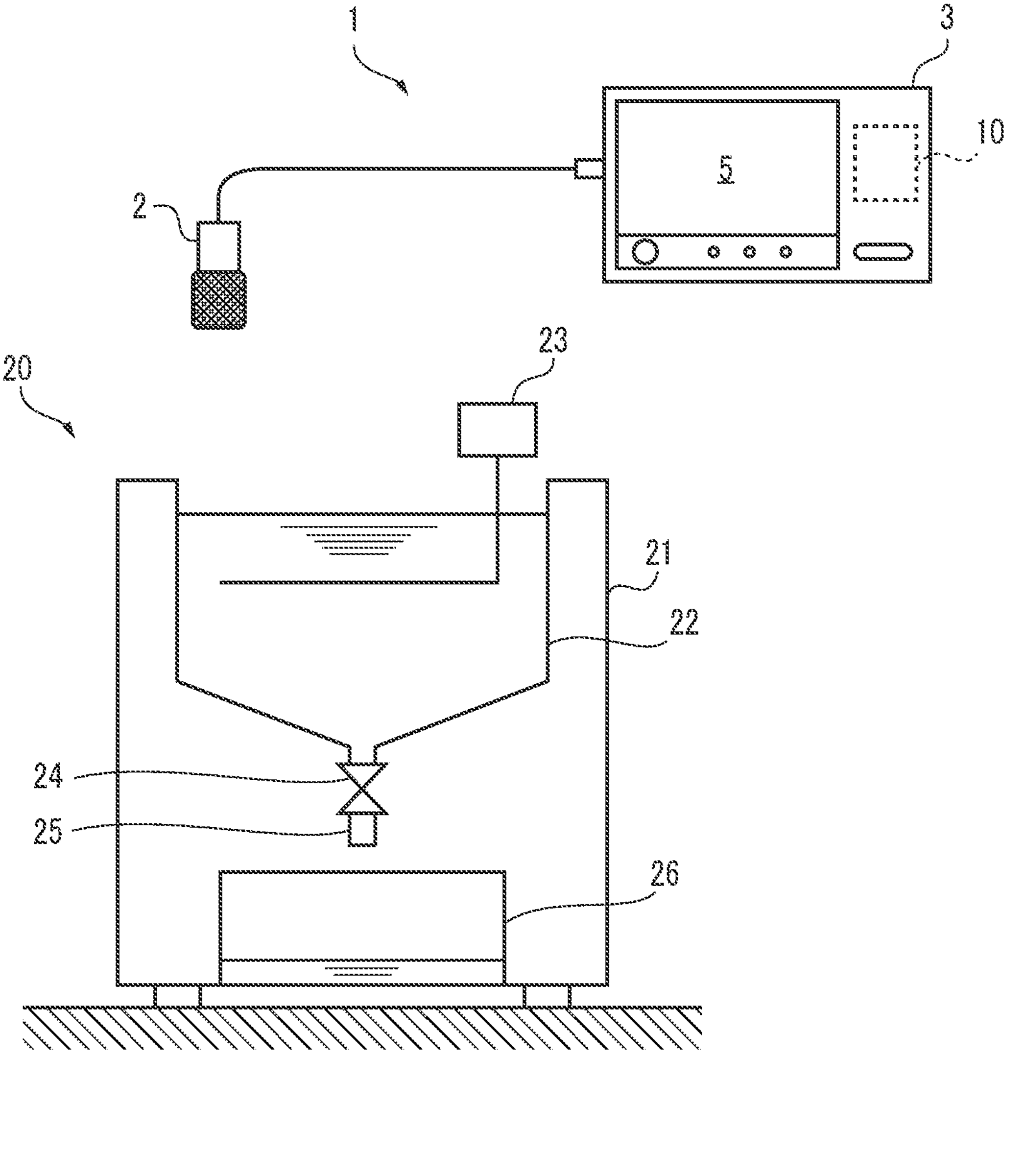
FIG. 1 is a diagram showing an overview of a deterioration prediction device and a fryer according to a first embodiment.

First, an overview of a deterioration prediction device 1 and a fryer 20 according to a first embodiment of the present invention is described with reference to FIG. 1. As shown in the drawing, the deterioration prediction device 1 is mainly configured from an acoustic data acquisition unit 2 ("acoustic data acquisition unit" of the present invention) and a processing unit 3. The acoustic data acquisition unit 2 is, e.g., a microphone having high directionality, and acquires acoustics from when a fried food article is cooked (sound of bubbles popping, etc.) using a fry oil ("oil and fat" of the present invention) accommodated in the fryer 20.

The acquired acoustics (referred to below as acoustic data) are transmitted to the processing unit 3. A feature quantity is extracted by the processing unit 3, and deterioration of the fry oil is analyzed from the feature quantity. The processing unit 3 (described in greater detail below) has a display unit 5, a control unit 10, etc.

The fryer 20 has a box-form cabinet 21 and is provided with an oil vat 22 for accommodating the fry oil therein. The temperature of the fry oil accommodated in the oil vat 22 can be adjusted using a heater 23. For example, when croquettes are being cooked, the fry oil is adjusted to 180° C.

An oil discharge pipe 25 is connected to the bottom surface of the oil vat 22 via a valve 24. The bottom surface of the oil vat 22 is formed in a funnel shape that is inclined downward in order to facilitate discharge of oil. Fry oil that has deteriorated is discharged as waste oil by opening the valve 24. A waste oil tank 26 is disposed below the oil discharge pipe 25 in order to accommodate the waste oil.

The oil vat 22 is assumed to be for a large-scale fryer used in an izakaya, etc., but is not limited thereto. Specifically, the oil vat 22 may be used in a smaller-scale fryer, or in a fried food article cooker for household use.

In the present embodiment, the acoustic data acquisition unit 2 is installed at a height of about 1 m from the fryer 20 (obliquely above the oil vat 22). Normally, because oil smoke is generated through cooking, a ventilation fan (not shown) for discharging the oil smoke to the outdoors is installed above the fryer 20. The acoustic data acquisition unit 2 may be attached to a side surface, etc., of the ventilation fan. The acoustic data acquisition unit 2 is preferably installed near the oil vat 22, either on the side surface of the cabinet 21 or on a wall surface, the ceiling, etc.

Figure 2:
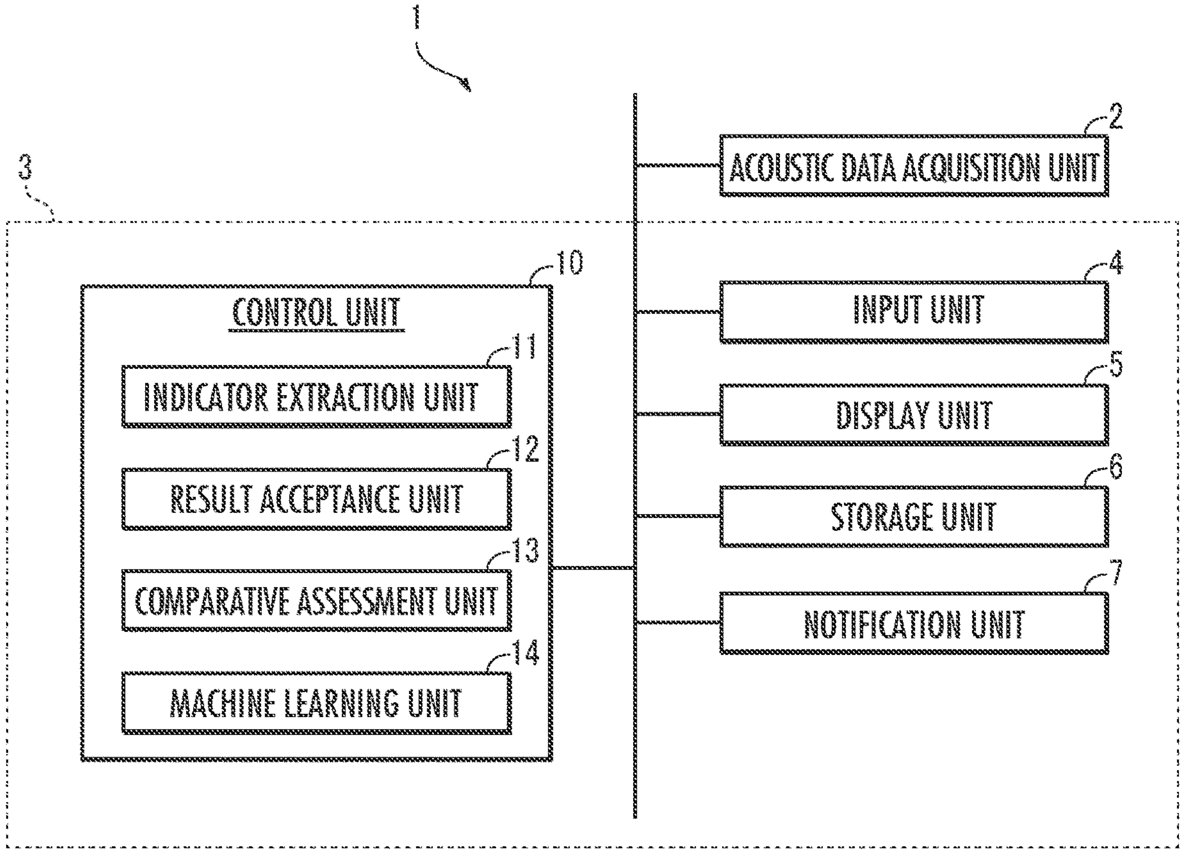
FIG. 2 is a function block diagram of the deterioration prediction device according to the first embodiment.

FIG. 2 is a function block diagram of the deterioration prediction device 1 according to the first embodiment.

The deterioration prediction device 1 is configured from the acoustic data acquisition unit 2 and the processing unit 3, and the processing unit 3 has an input unit 4, a display unit 5, a storage unit 6, a notification unit 7, and a control unit 10. First, the acoustic data acquisition unit 2 acquires acoustics from when croquettes, tempura, etc., are cooked A microphone may be used as the acoustic data acquisition unit 2, or the acoustic data acquisition unit 2 may record acoustics using a recording function of a video camera or a smartphone. For example, the acoustic data acquisition unit 2 acquires acoustic data for the cooking time of a fried food article at an audio sample rate of 48 kHz. In the acoustic data, because an operator creates noise by introducing and removing the fried food article, the acoustics occurring for ten seconds after the start of recording and for ten seconds before the end of recording are cut off.

When the fry oil deteriorates, fatty acids contained in the fry oil decompose, and the acoustics during cooking gradually change. An indicator extraction unit 11 of the control unit 10 extracts an indicator pertaining to the deterioration of the fry oil (referred to below as indicator data) from the acquired acoustic data, the indicator data being accepted by a result acceptance unit 12.

Because characteristics are often expressed by the frequency (frequency) of the acoustics during cooking, the frequency mean (f_mean), the frequency standard deviation (f_sd), the frequency median value (f_median), the frequency standard error (f_sem), and the frequency mode value (f_mode) are used as the indicator data.

Examples of other indicator data include the frequency first quartile (f_Q25) at a position 25% from the minimum frequency, the frequency third quartile (f_Q75) at a position 75% from the minimum frequency, the frequency interquartile range (f_IQR), the frequency centroid (f_cent), the frequency skewness (f_skewness), the frequency kurtosis (f_kurtosis), the frequency spectrum flat module (f_sfm), the frequency spectrum entropy (f_sh), the frequency spectrum precision (prec), the acoustic complexity index (d.ACI), the acoustic entropy (d.H), and the predominant frequency (dfnum). In analysis of the acoustics, seewave (sound analysis and synthesis) and ropls (PCA, PLS (-DA), and OPLS (-DA) for multivariate analysis) are used.

The control unit 10 specifically is a processor that controls and manages the entire deterioration prediction device 1, and is configured from a central processing unit (CPU) that executes a program in which a control procedure is defined. This program is stored in, e.g., the storage unit 6 or another external storage medium device.

The control unit 10 controls the entire processing unit 3 to execute the processes of the deterioration prediction device 1. For example, the control unit 10 activates the deterioration prediction device 1, based on a prescribed input operation performed by a user (shop employee). The prescribed input operation is, e.g., an operation for introducing a power supply of the deterioration prediction device 1, or an operation for setting a cooking time or the temperature of the fry oil.

The input unit 4 is a variety of switches that accept input operations from the user, and is configured from, e.g., operation buttons or operation keys. The input unit 4 is not limited to this configuration, and may be configured from a touch panel. The input unit 4 also accepts a prescribed input operation from the user before the processes are executed by the deterioration prediction device 1, and transmits a signal based on the input operation by the user to the control unit 10.

The display unit 5 displays various items for the user to perform the input operation. For example, when the user is to select the type of food product to be cooked, the display unit 5 displays types of food products, based on data relating to the types of food products that is stored in the storage unit 6. When the notification unit 7 notifies the user regarding the extent of deterioration of the fry oil, the display unit 5 displays an indication that the fry oil must be replaced, fulfilling an auxiliary role in notification.

The storage unit 6 is configured from a semiconductor memory or a magnetic memory, etc., and stores various information, a program for running the deterioration prediction device 1, etc. The storage unit 6 stores data relating to the food product being cooked in addition to the acquired acoustic data and a trained model. For example, the storage unit 6 stores correlation data indicating the correlation between the acoustic data and the extent of deterioration of the fry oil for each type of food product being handled. The storage unit 6 also stores threshold value information for notification, this information differing for each type of food product.

The notification unit 7 notifies the user when it is assessed that the extent of deterioration of the fry oil has exceeded a prescribed threshold value. Thus, the notification unit 7 notifies the user of a replacement timing for the fry oil. The “replacement timing” is a timing at which the fry oil is to be actually replaced (a display indicating that “a replacement period has arrived,” etc.). The notification unit 7 also can issue a notification regarding the current extent of deterioration of the fry oil (a display indicating that “the current extent of deterioration is 50%,” etc.), and moreover can issue notification regarding the remaining time in which the fry oil can be used as estimated from the extent of deterioration (a display indicating that the fry oil is “usable for 20 more hours,” etc.).

A speaker is one example of the notification unit 7. The notification unit 7 can issue notification through speech guidance, alarms, or other auditory methods. The notification unit 7 may also issue notification through visual methods carried out through: display of images, characters, or colors; emission of light; etc. For example, notification may be issued by displaying images or characters using the display unit 5, or through use of LEDs or other light-emitting elements. The notification by the notification unit 7 is not limited to visual or auditory methods; a combination thereof may be used, or a discretionary method by which the user can objectively recognize the replacement period of the fry oil, such as vibration, may be used.

A comparative assessment unit 13 of the control unit 10 compares the acquired acoustic data and correlation data that corresponds to the type of food product being cooked using the fry oil, and assesses the extent of deterioration of the fry oil. The acoustics generated during cooking using the fry oil accommodated in the oil vat 22 depend on the type of food product being cooked. The optimal replacement period for the fry oil also differs for each type of food product being cooked.

The correlation data is stored in advance in the storage unit 6. The comparative assessment unit 13 acquires the correlation data from the storage unit 6 during comparison and assesses the extent of deterioration of the fry oil. The correlation data may be created by a machine learning unit 14, but does not necessarily need to be created within the deterioration prediction device 1; correlation data provided from the outside may be used.

The control unit 10 controls the notification unit 7 in order to issue a notification when it is assessed that the extent of deterioration of the fry oil has exceeded a prescribed threshold value that corresponds to the type of food product. The threshold value is predetermined for each type of food product. The threshold value may be changed, as appropriate, by the user. A plurality of threshold values may also be set.

Figure 3:
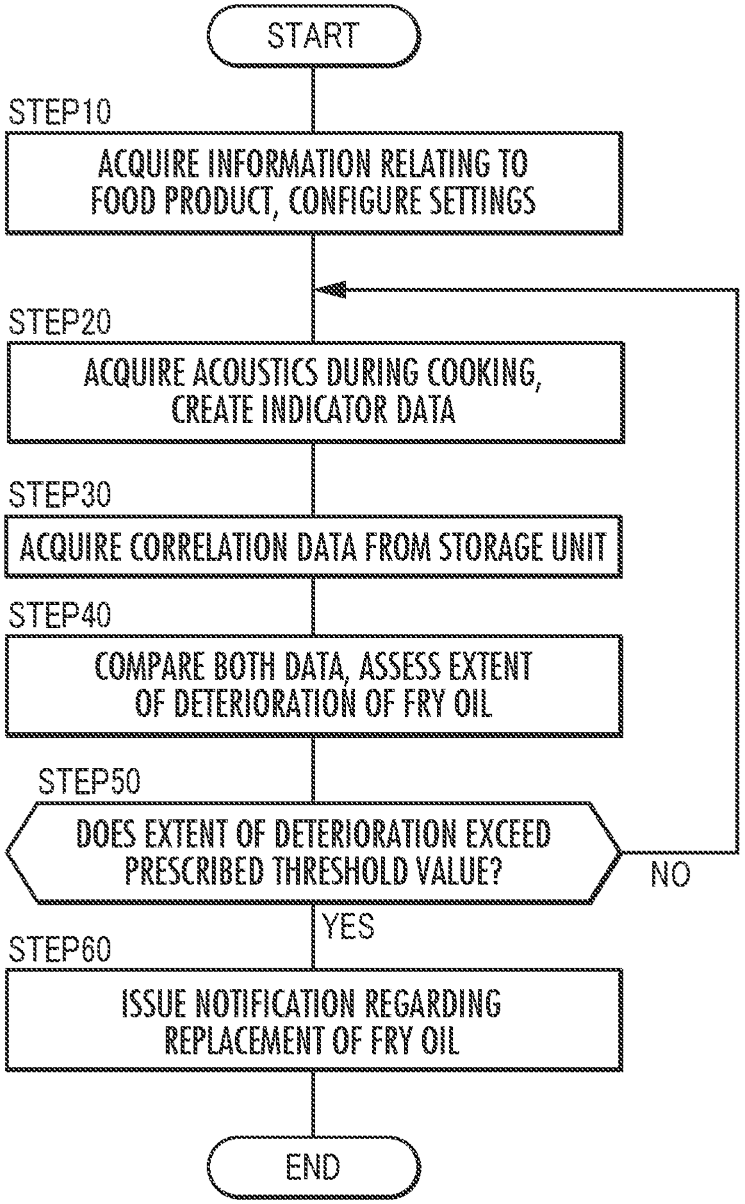
FIG. 3 is a flow chart for assessment of the deterioration of a fry oil performed by the deterioration prediction device.

Next, a flow chart for assessment of the deterioration of the fry oil performed by the deterioration prediction device 1 is described with reference to FIG. 3. FIG. 3 is a flow chart showing a case where a threshold value that can be used as a guidance for replacement of the fry oil is set in advance.

First, the user acquires information relating to the food product to be cooked and configures necessary settings (STEP 10). Because the acoustics during cooking differ depending on whether the food product for the fried food article is croquettes or tempura, the deterioration prediction device 1 is set according to the fried food article. The process then advances to STEP 20.

In STEP 20, indicator data is created from the acoustics during cooking. Specifically, the acoustics during cooking (acoustic data) are acquired by the acoustic data acquisition unit 2 and transmitted to the processing unit 3, and indicator data such as the frequency mean (f_mean) is created. The process then advances to STEP 30.

In STEP 30, the correlation data is acquired from the storage unit. The correlation data is necessary when assessing the extent of deterioration of the fry oil in subsequent steps. The process then advances to STEP 40.

In STEP 40, the data are compared and the extent of deterioration of the fry oil is assessed. Specifically, the comparative assessment unit 13 of the control unit 10 compares the acoustic data and the correlation data. The process then advances to STEP 50.

An assessment is then made as to whether the extent of deterioration of the fry oil has exceeded a prescribed threshold value (STEP 50). The threshold value differs in accordance with the food product for the fried food article. If the threshold value is exceeded, the process advances to STEP 60; if the threshold value is not exceeded, the process returns to STEP 20.

If the extent of deterioration of the fry oil has exceeded the prescribed threshold value (YES in STEP 50), the user is notified of this circumstance (STEP 60). Specifically, a notification is issued by the notification unit 7 in order to prompt the user to replace the fry oil. The series of processes then ends.

Second Embodiment

Next, an overview of a deterioration prediction system 100 according to a second embodiment of the present invention is described with reference to FIG. 4. The deterioration prediction system 100 is mainly configured from a detection device 30 and a machine learning device 40. The detection device 30 and the machine learning device 40 are connected by a network NW and are capable of mutually transmitting and receiving various data.

The detection device 30 has an acoustic data acquisition unit 2, an input unit 4, a display unit 5, a storage unit 6, a notification unit 7, a communication unit 8, and a control unit 10. The control unit 10 has a comparative assessment unit 13. Other than the configurations of the communication unit 8, the configuration of the detection device 30 is identical to that of the processing unit 3 in the first embodiment; therefore, the identical portions are not described here.

In the detection device 30, when acoustics from when croquettes, tempura, etc., are cooked are acquired by the acoustic data acquisition unit 2, the comparative assessment unit 13 compares the acquired acoustic data and correlation data that corresponds to the type of food product being cooked, and assesses the extent of deterioration of the fry oil.

The communication unit 8 ("first communication unit" of the present invention) automatically transmits the acoustic data to the machine learning device 40 via the network NW. This communication may be wired, or may be Wi-Fi®, Bluetooth®, or another form of wireless communication. In the deterioration prediction system 100, because it is preferable for only the detection device 30 to be located within a shop or a factory (near the oil vat 22), the device can be reduced in size.

The machine learning device 40 has a communication unit 48 ("second communication unit" of the present invention) and a trained model creation unit 50. The acoustic data is automatically received by the communication unit 48 of the machine learning device 40. The machine learning device 40 may be installed at a position that is set apart from the fryer 20. As shall be apparent, the detection device 30 and the machine learning device 40 may constitute an integrated system.

The trained model creation unit 50 has an indicator extraction unit 51, a storage unit 52, and a calibration curve creation unit 53. The indicator extraction unit 51 extracts indicator data pertaining to deterioration of the fry oil from the received acoustic data, the indicator data being stored in the storage unit 52. The calibration curve creation unit 53 carries out "supervised learning" and creates a calibration curve (model formula) through linear regression analysis from the stored indicator data (explanatory variable).

Examples of classes of the linear regression (analysis) include single regression, multiple regression, partial least squares (PLS) regression, and orthogonal partial least squares (OPLS) regression; one or more selected from these classes can be used.

Single regression is a method for predicting one target variable using one explanatory variable, and multiple regression is a method for predicting one target variable using a plurality of explanatory variables. (Orthogonal) partial least squares regression is a method for extracting a main component that is a small number of feature quantities (obtained by main component analysis of only explanatory variables) such that the covariance of the target variable with the main component is maximized. (Orthogonal) partial least squares regression is suitable when the number of explanatory variables is greater than the number of samples, and when the correlation between the explanatory variables is strong.

Figures 5A, 5B:
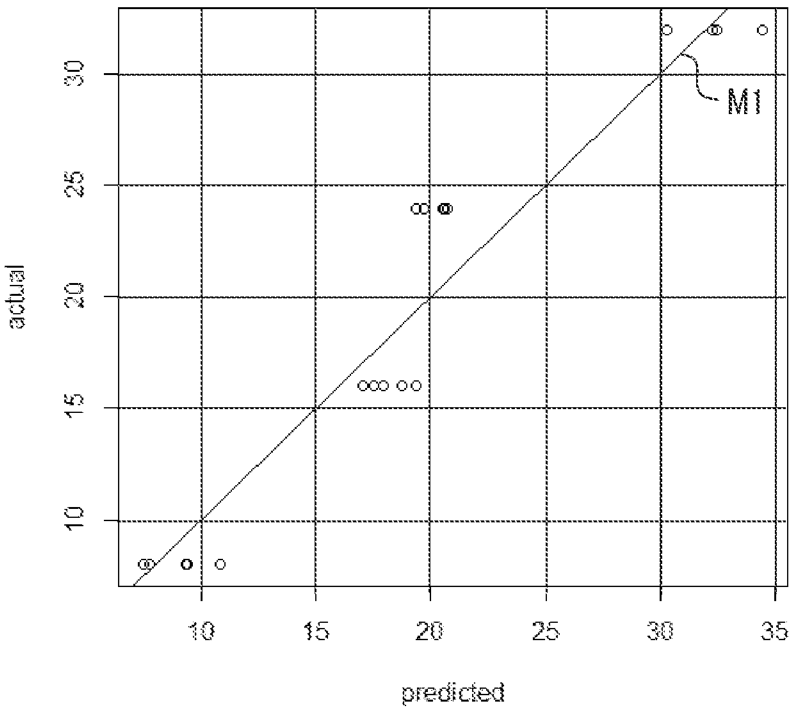
FIG. 5A is a graph showing the relationship between a calibration curve obtained through machine learning (single regression) and heating times in test data.
FIG. 5B is a table listing the mean predicted values and the standard deviations in FIG. 5A.

FIGS. 5A and 5B show the relationship between a calibration curve obtained through machine learning and heating times (predicted values and actual measured values) in test data.

The straight line M1 in FIG. 5A is a calibration curve (model formula) obtained by single regression analysis according to the frequency mean (f_mean). In this graph, the horizontal axis represents predicted values for the heating time [h], and the vertical axis represents the actual measured values for the heating time [h], with the circle marks in the graph being plots of the predicted values obtained from the frequency mean (f_mean).

FIG. 5B shows a list of heating times in a current instance (actual measured values for frying time), five mean predicted values, and standard deviations. For example, the mean predicted value with respect to an actual measured value of 8 [h] for the heating time was 8.9 [h], and the standard deviation in this case was 1.4. Because the predicted values are roughly near the straight line M1 (refer to FIG. 5A) and variation is comparatively low, it was confirmed that the calibration curve obtained through single regression analysis has a certain degree of precision.

Figures 6A, 6B:
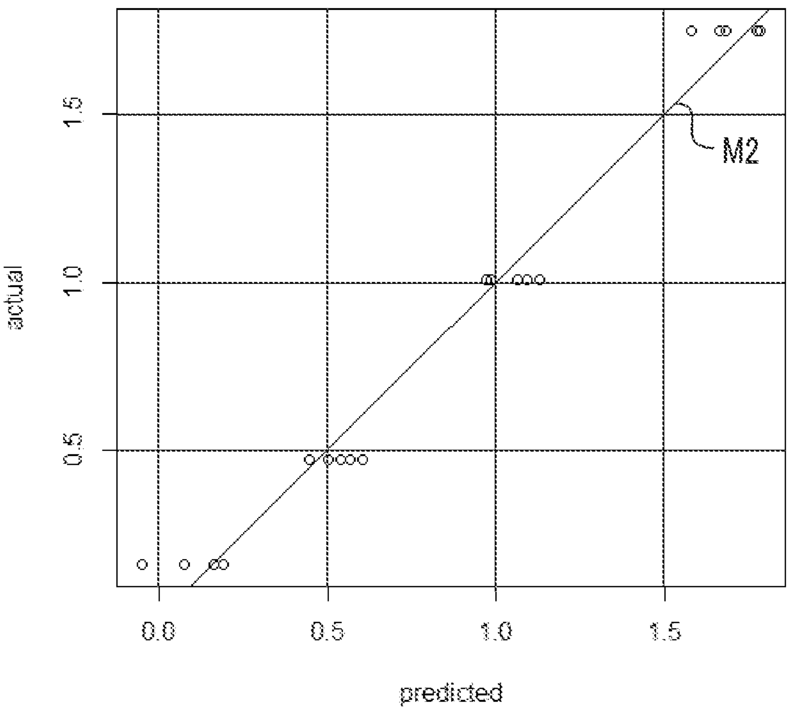
FIG. 6A is a graph showing the relationship between a calibration curve obtained through machine learning (multiple regression) and acid values in test data.
FIG. 6B is a table listing the actual measured values, the mean predicted values, and the standard deviations in FIG. 6A.

FIGS. 6A and 6B show the relationship between a calibration curve obtained through machine learning and acid values (predicted values and actual measured values) in test data.

The straight line M2 in FIG. 6A is a calibration curve (model formula) obtained by multiple regression analysis according to the frequency mean (f_mean) and the frequency spectrum flat module (f_sfm). In this graph, the horizontal axis represents predicted values for the acid value, and the vertical axis represents the actual measured values for the acid value, with the circle marks in the graph being plots of the predicted values for the acid value obtained from the frequency mean (f_mean) and the flat module (f_sfm).

FIG. 6B shows a list of heating times in a current instance, actual measured values for the acid value, five mean predicted values, and standard deviations. For example, the actual measured value for the acid value with respect to an actual measured value of 8 [h] for the heating time was 0.16, the mean predicted value was 0.11, and the standard deviation in this case was 0.10. Because the predicted values for the acid value are present on the straight line M2 (refer to FIG. 6A) and variation is low, it was confirmed that the calibration curve obtained through multiple regression analysis has a high degree of precision.

Figures 7A, 7B:
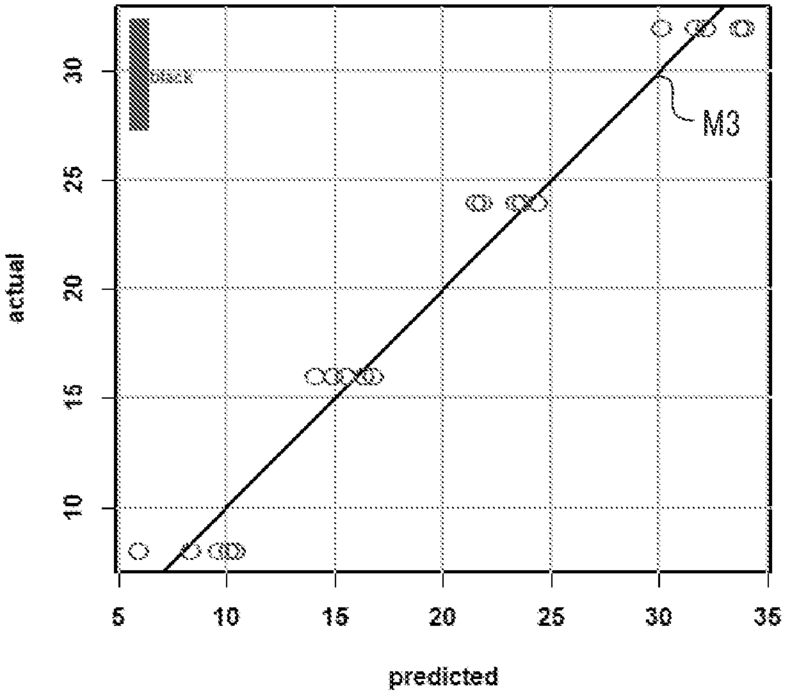
FIG. 7A is a graph showing the relationship between a calibration curve obtained through machine learning (OPLS) and heating times in test data.
FIG. 7B is a table listing the mean predicted values and the standard deviations in FIG. 7A.

FIGS. 7A and 7B show the relationship between a calibration curve obtained through machine learning and heating times (predicted values and actual measured values) in test data.

The straight line M3 in FIG. 7A is a calibration curve (model formula) obtained by orthogonal partial least squares (OPLS) analysis. In this graph, the horizontal axis represents predicted values for the heating time [h], and the vertical axis represents the actual measured values for the heating time [h], with the circle marks in the graph being plots of the predicted values obtained from the frequency mean (f_mean).

FIG. 7B shows a list of heating times in a current instance (actual measured values for frying time), five mean predicted values, and standard deviations. For example, the mean predicted value with respect to an actual measured value of 8 [h] for the heating time was 9.0 [h], and the standard deviation in this case was 1.8. Because the predicted values are present on the straight line M3 (refer to FIG. 7A) and variation is comparatively low, it was confirmed that the calibration curve obtained through orthogonal partial least squares has a certain degree of precision.

Figures 8A, 8B:
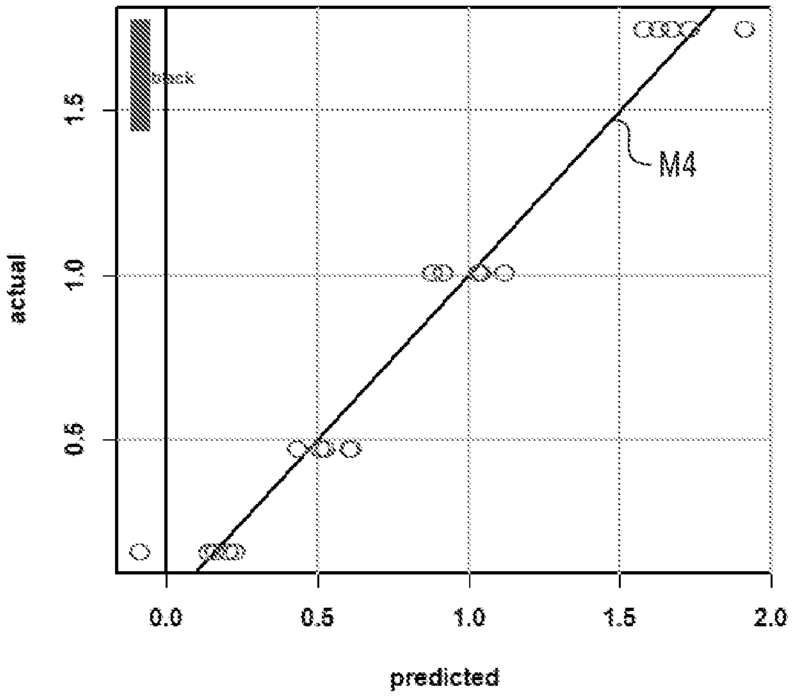
FIG. 8A is a graph showing the relationship between a calibration curve obtained through machine learning (OPLS) and acid values in test data.
FIG. 8B is a table listing the actual measured values, the mean predicted values, and the standard deviations in FIG. 8A.

FIGS. 8A and 8B show the relationship between a calibration curve obtained through machine learning and acid values (predicted values and actual measured values) in test data. The "acid value" is measured according to Standard Methods for the Analysis of Fats, Oils, and Related Materials 2.3.1-2013.

The straight line M4 in FIG. 8A is a calibration curve (model formula) obtained by orthogonal partial least squares (OPLS) analysis. In this graph, the horizontal axis represents predicted values for the acid value, and the vertical axis represents the actual measured values for the acid value, with the circle marks in the graph being plots of the predicted values for the acid value obtained from the indicator data such as the frequency mean (f_mean).

FIG. 8B shows a list of heating times in a current instance, actual measured values for the acid value, five mean predicted values, and standard deviations. For example, the actual measured value for the acid value with respect to an actual measured value of 8 [h] for the heating time was 0.16, the mean predicted value was 0.13, and the standard deviation in this case was 0.12. Because there is little variation in the predicted values for the acid value, it was confirmed that the calibration curve obtained through orthogonal partial least squares analysis has a high degree of precision.

Figures 9A, 9B:
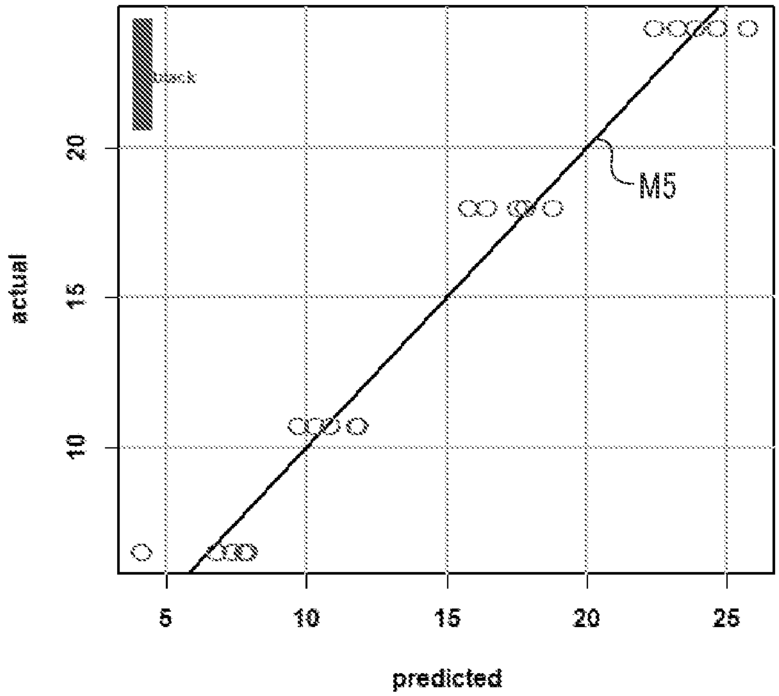
FIG. 9A is a graph showing the relationship between a calibration curve obtained through machine learning (PLS) and colors in test data.
FIG. 9B is a table listing the actual measured values, the mean predicted values, and the standard deviations in FIG. 9A.

FIGS. 9A and 9B show the relationship between a calibration curve obtained through machine learning and colors (predicted values and actual measured values) in test data. The "color" is the color tone of the fry oil and indicates "Y+10R" measured according to Standard Methods for the Analysis of Fats, Oils, and Related Materials 2.2.1.1-1996.

The straight line M5 in FIG. 9A is a calibration curve (model formula) obtained by partial least squares (PLS) analysis. In this graph, the horizontal axis represents predicted values for the color, and the vertical axis represents the actual measured values for the color, with the circle marks in the graph being plots of the predicted values for the color obtained from the indicator data such as the frequency mean (f_mean).

FIG. 9B shows a list of heating times in a current instance, actual measured values for the color, five mean predicted values, and standard deviations. For example, the actual measured value for the color with respect to an actual measured value of 8 [h] for the heating time was 6.5, the mean predicted value was 6.9, and the standard deviation in this case was 1.6. Because there is comparatively little variation in the predicted values for the color, it was confirmed that the calibration curve obtained through partial least squares analysis has a certain degree of precision.

Figures 10A, 10B:
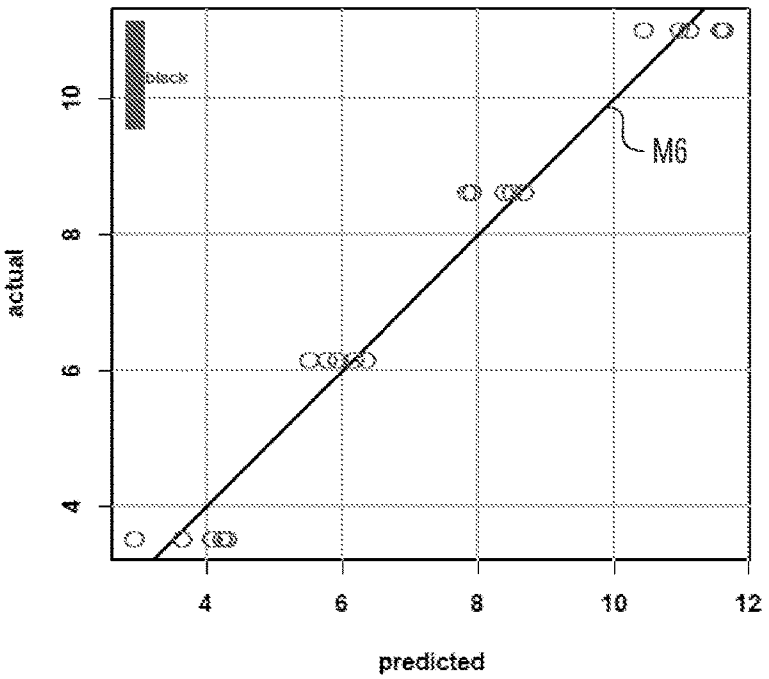
FIG. 10A is a graph showing the relationship between a calibration curve obtained through machine learning (PLS) and rates of increase in viscosity in test data.
FIG. 10B is a table listing the actual measured values, the mean predicted values, and the standard deviations in FIG. 10A.

FIGS. 10A and 10B show the relationship between a calibration curve obtained through machine learning and rates of increase in viscosity (predicted values and actual measured values) in test data. The "viscosity" is a numeric value indicating the degree of stickiness (viscous properties) of the fry oil as measured by a commercially available viscometer, e.g., an E-type viscosity (TVE-25H: made by Toki Sangyo KK); in this instance, the rate of increase in viscosity (%) with respect to the heating time is examined.

Deterioration of the fry oil advances and the viscosity of the fry oil increases as fried food articles are repeatedly fried using the fry oil, the measurement value for the viscosity when the fry oil is first used (viscosity during start of use) being designated as Vs. The "rate of increase in viscosity" is defined as the ratio of the amount of increase in viscosity (=Vt−Vs) to Vs, where Vt is the measurement value for the viscosity after the start of use.

The straight line M6 in FIG. 10A is a calibration curve (model formula) obtained by partial least squares (PLS) analysis. In this graph, the horizontal axis represents predicted values for the rate of increase in viscosity [%], and the vertical axis represents the actual measured values for the rate of increase in viscosity [%], with the circle marks in the graph being plots of the predicted values for the rate of increase in viscosity obtained from the indicator data such as the frequency mean (f_mean).

FIG. 10B shows a list of heating times in a current instance, actual measured values for the rate of increase in viscosity, five mean predicted values, and standard deviations. For example, the actual measured value for the rate of increase in viscosity with respect to an actual measured value of 8 [h] for the heating time was 3.52, the mean predicted value was 3.87, and the standard deviation in this case was 0.57. Because there is little variation in the plotted predicted values for the rate of increase in viscosity, it was confirmed that the calibration curve obtained through partial least squares analysis has a high degree of precision.

As described above, the calibration curve creation unit 53 creates a calibration curve through linear regression analysis from the indicator data, and any of single regression, multiple regression, partial least squares (PLS) regression, and orthogonal partial least squares (OPLS) regression may be used as the linear regression. The calibration curve actually created makes it possible to accurately predict and assess deterioration of the fry oil from the indicator data relating to acoustics, with high precision for the extent of deterioration, in relation to results in which the fry oil is evaluated using the acid value, the color, the rate of increase in viscosity, etc., these parameters changing according to the heating time.

Figure 4:
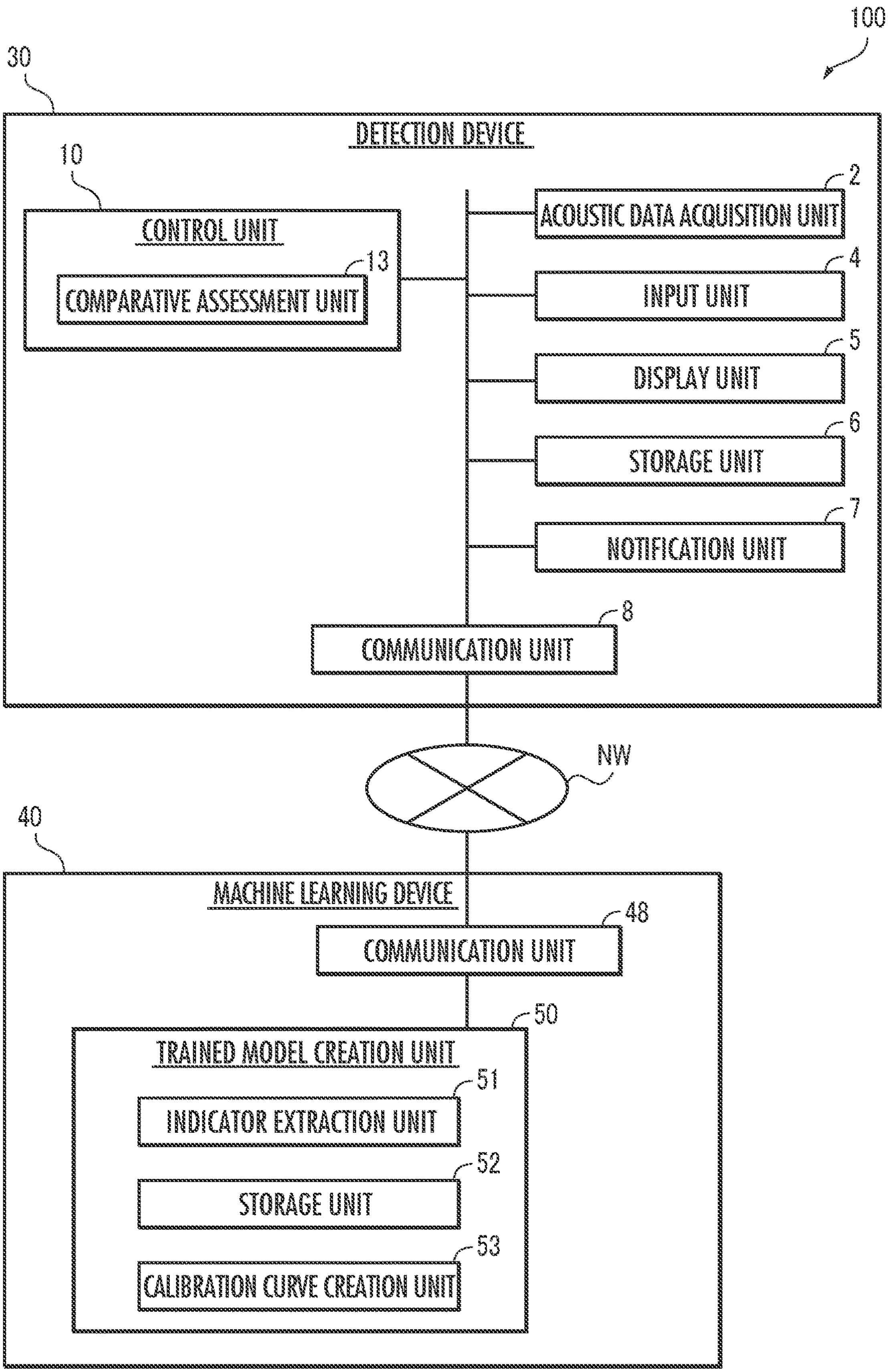
FIG. 4 is a function block diagram of a deterioration prediction device (deterioration prediction system) according to a second embodiment.

In the deterioration prediction system 100 shown in FIG. 4, the machine learning device 40 may be installed at a remote location that is set apart from a shop, and the detection device 30 and the machine learning device 40 may be related to a detection server and a machine learning server, respectively.

In such instances, the shop-side detection server is provided with at least: an acoustic data acquisition unit that acquires acoustic data from when a fried food article is cooked; a communication unit that transmits and receives various data (acoustic data, assessment results, etc.) to and from the machine learning server; and a notification unit that issues a notification regarding the extent of deterioration of the fry oil, a replacement timing, etc., based on the assessment results.

The machine learning server at the remote location is provided with at least: a communication unit that transmits and receives various data to and from the detection server; a trained model creation unit that extracts an indicator pertaining to deterioration of the fry oil from the received acoustic data, that carries out machine learning by linear regression using the indicator, and that creates a trained model with which deterioration of the fry oil can be assessed; a storage unit that stores the created trained model; and an assessment unit that assesses the extent of deterioration of the fry oil using the trained model.

According to this configuration, the trained model creation unit carries out machine learning on the machine-learning-server side through use of received acoustic data and creates a trained model. In addition, the assessment unit assesses the extent of deterioration of the fry oil using the trained model and transmits the assessment results to the detection-server side. Moreover, the notification unit issues a notification on the detection-server side with regard to a replacement timing for the fry oil, based on the received assessment results. Thus, roles can be assigned such that the acoustic data is received and assessed on the machine-learning-server side, and such that the assessment results are returned to the detection server.

The trained model is created on the machine-learning-server side, and is, for example, updated each time new acoustic data is acquired. This makes it possible for the side with the shop having the detection server to acquire the replacement timing for the fry oil without requiring transmission or reception of the trained model, which has a comparatively high data volume.

Third Embodiment

Next, an overview of an oil and fat replacement system 200 according to a third embodiment of the present invention is described with reference to FIG. 11.

Figure 11:
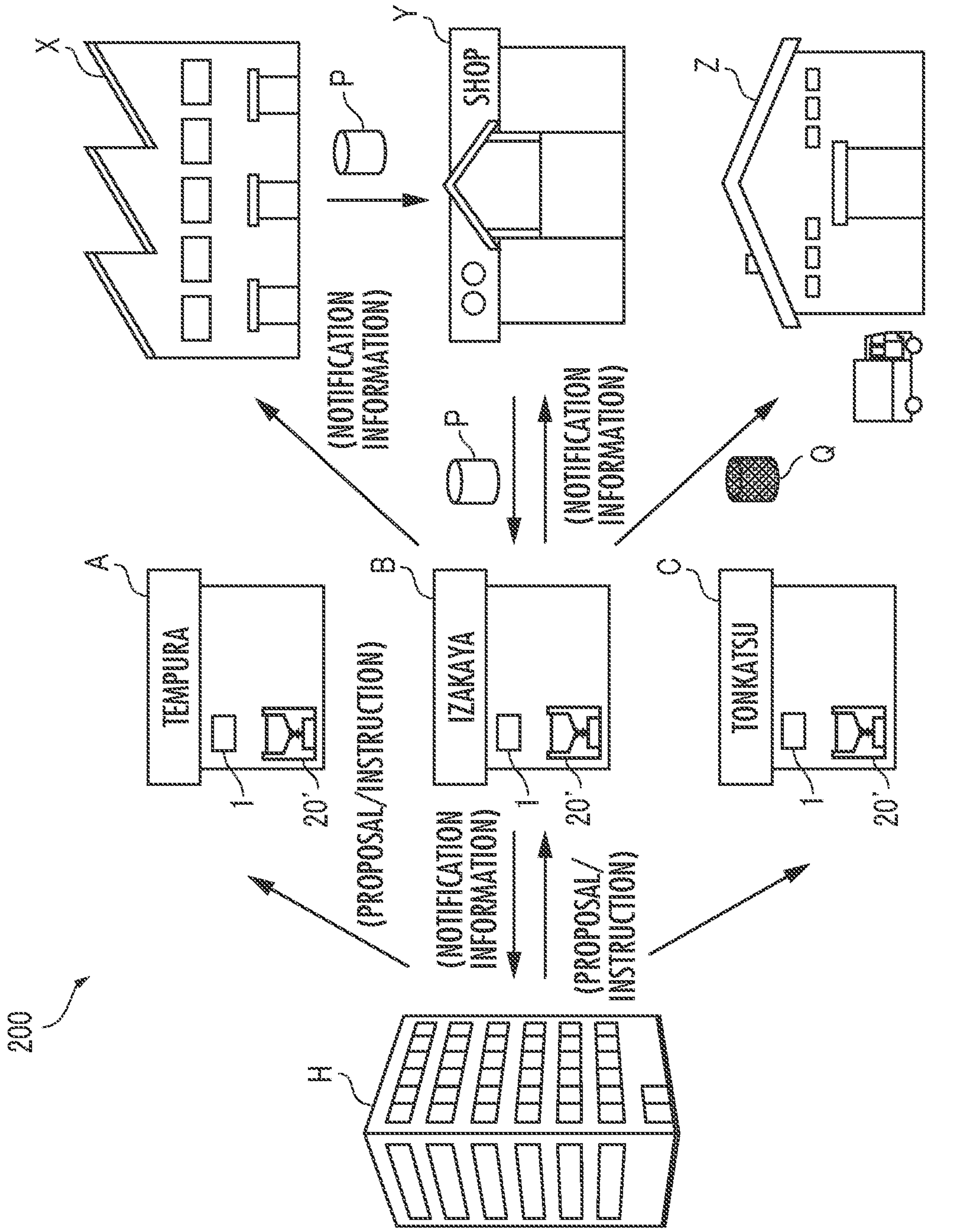
FIG. 11 is a drawing illustrating an oil and fat replacement system according to a third embodiment.

FIG. 11 is a drawing illustrating an overview of the oil and fat replacement system 200. As shown in the drawing, the oil and fat replacement system 200 is configured from: shops A to C, each of which is provided with a deterioration prediction device 1 and a fryer 20'; a general headquarters H that supervises the shops A to C; a fry oil manufacturer (oil and fat maker) X used by the shops A to C; a vendor (wholesaler or vendor) Y; and a collector Z that collects waste oil. Because the oil and fat maker may also sell directly to customers, the vendor Y is a general concept that includes an oil and fat maker.

In the first embodiment, when it is assessed that the extent of deterioration of the fry oil has exceeded a prescribed threshold value, the notification unit 7 of the deterioration prediction device 1 notifies a user of this circumstance using a speaker, the display unit 5, etc.; however, in the present embodiment, the notification unit 7 also outputs notification information relating to the extent of deterioration of the fry oil in addition to issuing this notification. The notification information may indicate that the extent of deterioration of the fry oil has exceeded the threshold value, but may also include advance notice indicating that the extent of deterioration will imminently exceed the threshold value.

As indicated in the drawing, when the general headquarters H is alerted with regard to notification information from the shop B (izakaya), the general headquarters H analyzes the number of times the notification information has been received, the frequency with which the notification information has been received, etc., and issues a proposal or an instruction to not only the shop B but also the shop A (tempura shop) and the shop C (tonkatsu shop) with regard to whether the method for using the fry oil is suitable, whether the fry oil is being replaced as appropriate, whether the fry oil is being wasted, etc.

The general headquarters H may be in a position to manage not only a plurality of shops but also a plurality of factories in which fryers are installed. The general headquarters H may also manage a plurality of on-site fryers that are present in the shops or factories.

The fry oil manufacturer X and the vendor Y are also alerted with regard to the notification information. The manufacturer X receives the notification information and produces a plan for manufacturing or selling the fry oil. The vendor Y receives the notification information, orders new fry oil, and buys fry oil P from the manufacturer X. The vendor Y supplies the new fry oil P to the shop B (and, as necessary, to the shop A and the shop C).

The fry oil collector Z (which may also be the manufacturer X) is furthermore alerted with regard to the notification information. The collector Z receives the notification information and makes preparations to collect waste oil Q. For example, upon receiving the notification information a prescribed number of times, the collector Z visits the shop B and collects the waste oil Q from the oil vat 22 of the fryer 20'.

A cleaning work provider (not shown) may furthermore be alerted with regard to the notification information. The cleaning work provider receives the notification information, visits the shop B, and cleans the interior of the oil vat 22 of the fryer 20' or the vicinity of the oil vat 22. Thus, in the oil and fat replacement system 200, operations from supply of fry oil to collection of waste oil, and even cleaning, can be carried out promptly for the shops A to C.

When replacement of the fry oil within the shops is automated, based on the notification content, the load on a user (shop employee) is further reduced. The replacement of the fry oil is automatically started when notification information indicating that the extent of deterioration of the fry oil has exceeded the threshold value is outputted.

Fourth Embodiment

Finally, an overview of a fryer system 300 according to a fourth embodiment of the present invention is described with reference to FIG. 12.

Figure 12:
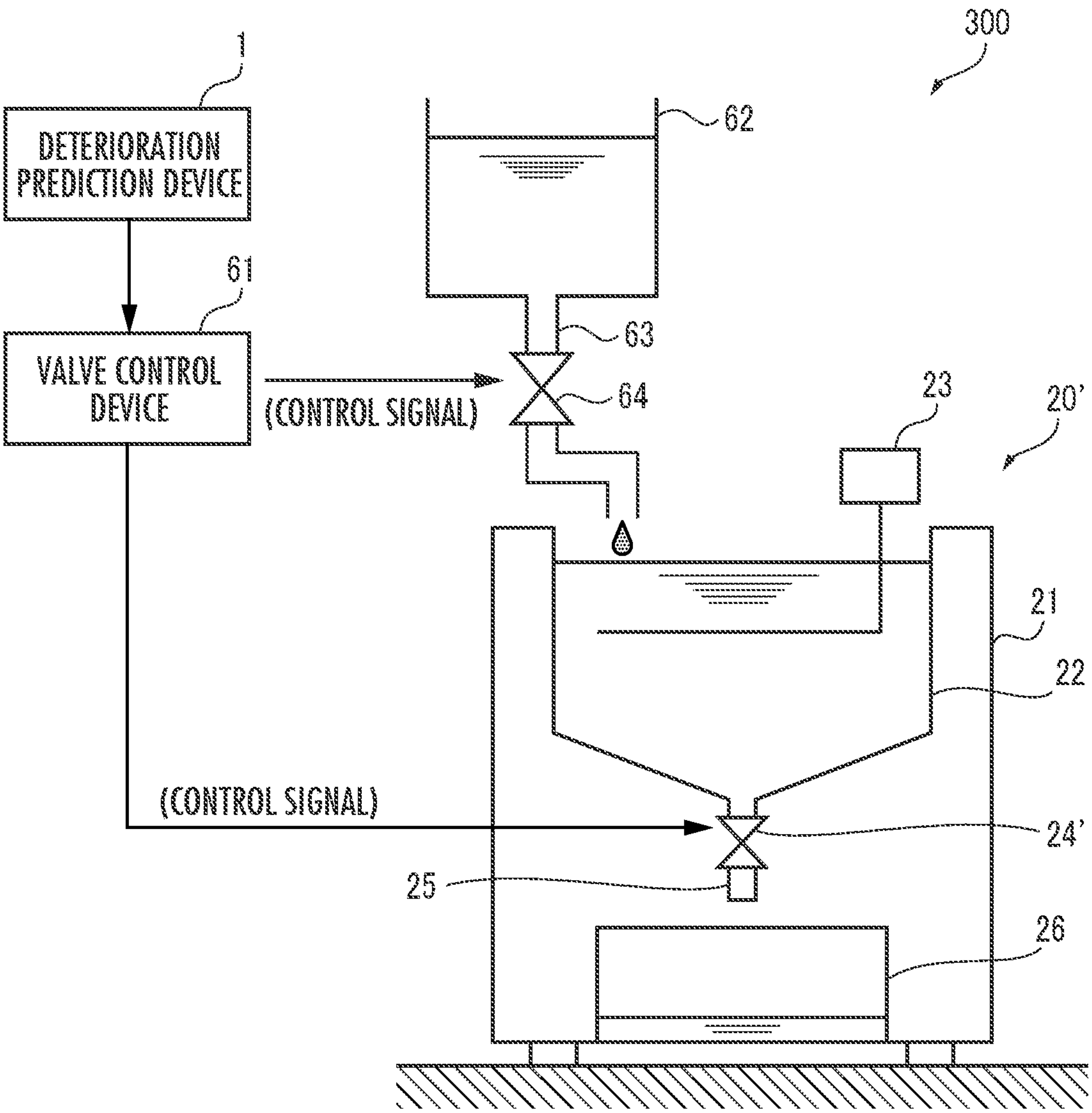
FIG. 12 is a diagram showing a fryer system according to a fourth embodiment.

FIG. 12 shows a deterioration prediction device 1 and a fryer 20' that constitute the fryer system 300 of the present embodiment. Portions of the fryer 20' that are identical in configuration to those of the fryer 20 in the first embodiment are associated with the same reference symbols, and the identical portions are not described here.

As shown in the drawing, a valve control device 61 ("valve control unit" of the present invention) and a new oil tank 62 are installed near the fryer 20'. Unused fry oil is accommodated in the new oil tank 62, and the fry oil is supplied to the oil vat 22 via an oil supply pipe 63.

Upon receiving, from the deterioration prediction device 1, notification information indicating that the fry oil is to be replaced (has reached or exceeded the threshold value), the valve control device 61 first transmits a control signal to a valve 24' to open the valve 24'. The waste oil is thereby automatically discharged to the waste oil tank 26 via the oil discharge pipe 25.

After sufficient time has elapsed, the valve control device 61 again transmits control signal to the valve 24' to close the valve 24'. The valve control device 61 then transmits a control signal to a valve 64 provided partway along the oil supply pipe 63 to open the valve 64. The new oil is thereby automatically supplied to the oil vat 22. The amount of new oil supplied may be detected by a liquid level sensor in the new oil tank 62, or the valve 64 may be opened for a prescribed time.

According to the present embodiment, the valve control device 61 controls the valves 24', 64, based on notification information transmitted from the deterioration prediction device 1, thereby making it possible to automatically discharge fry oil during use. Furthermore, the valve control device 61 performs a control to automatically supply new oil from the new oil tank 62, thereby making it possible to reduce the workload through which a user confirms the extent of deterioration of the fry oil, discharges waste oil, and supplies new oil.

The deterioration prediction device, deterioration prediction system, and oil and fat replacement system described above are merely examples of embodiments of the present invention; these embodiments can be changed, as appropriate, in accordance with the application, objective, etc. In this instance, examples are illustrated in which the frequency mean (f_mean) and the frequency spectrum flat module (f_sfm) are extracted from the acoustic data to perform regression analysis; however, the frequency standard deviation (f_sd), the predominant frequency (dfnum), etc., can also be applied in predicting deterioration of the fry oil.

In the deterioration prediction system, the roles fulfilled by the various constituent devices can be changed. The deterioration prediction system 100 shown in FIG. 4 is divided into the detection device 30 and the machine learning device 40 as separate devices, but the acoustic data and the trained model have a high data volume, and communication is both time- and cost-intensive. Therefore, a control device, that is capable of receiving notification information indicating, inter alia, the extent of deterioration of the fry oil from the detection device from a remote location, and of commanding a detection device having a machine learning unit incorporated therein, may be newly provided.

KEY

1 Deterioration prediction device
2 Acoustic data acquisition unit
3 Processing unit
4 Input unit
Display unit
6 Storage unit
7 Notification unit
8 Communication unit (first communication unit)
10 Control unit
11, 51 Indicator extraction unit
12 Result acceptance unit
13 Comparative assessment unit
14 Machine learning unit
20, 20' Fryer
21 Cabinet
22 Oil vat
23 Heater
24, 24', 64 Valve
25 Oil discharge pipe
26 Waste oil tank
30 Detection device
40 Machine learning device
48 Communication unit (second communication unit)
50 Trained model creation unit
52 Storage unit
53 Calibration curve creation unit
61 Valve control device
62 New oil tank
63 Oil supply pipe
100 Deterioration prediction system
200 Oil and fat replacement system
300 Fryer system

The invention claimed is:

1. A deterioration prediction device that predicts the extent of deterioration of an edible oil and fat, the deterioration prediction device comprising:

an acoustic data acquisition unit that acquires acoustic data from when a fried food article is cooked using the oil and fat, which is accommodated in an oil vat;

an indicator extraction unit that extracts an indicator pertaining to deterioration of the oil and fat from the acoustic data acquired by the acoustic data acquisition unit; and an assessment unit that assesses the extent of deterioration of the oil and fat, based on the indicator extracted by the indicator extraction unit, wherein the acoustic data acquisition unit acquires the acoustic data at cooking of the fried food article, the deterioration prediction device further comprises a storage unit having a memory which stores correlation data indicating a correlation between the acoustic data and the extent of deterioration of the oil and fat for each type of the fried food article being handled, and the assessment unit detects the extent of deterioration of the oil and fat in accordance with the correlation data stored in the memory.

2. The deterioration prediction device according to claim 1, furthermore comprising a notification unit that issues a notification regarding the extent of deterioration of the oil and fat or regarding a replacement timing for the oil and fat, the notification unit issuing the notification when it is assessed by the assessment unit, based on the extent of deterioration of the oil and fat, that a predetermined replacement threshold value has been exceeded.

3. The deterioration prediction device according to claim 1, wherein the indicator is one or more selected from the frequency mean, the frequency standard deviation, the frequency median value, the frequency standard error, the frequency mode value, the frequency first quartile, the frequency third quartile, the frequency interquartile range, the frequency centroid, the frequency skewness, the frequency kurtosis, the frequency spectrum flat module, the frequency spectrum entropy, the frequency spectrum precision, the acoustic complexity index, the acoustic entropy, and the predominant frequency.

4. A deterioration prediction method for predicting the extent of deterioration of an edible oil and fat, the method comprising an acoustic data acquisition step for acquiring acoustic data from when a fried food article is cooked using the oil and fat, which is accommodated in an oil vat, an indicator extraction step for extracting an indicator pertaining to deterioration of the oil and fat from the acoustic data acquired in the acoustic data acquisition step, and an assessment step for assessing the extent of deterioration of the oil and fat, based on the indicator extracted in the indicator extraction step, wherein the acoustic data acquisition step includes acquiring the acoustic data at cooking of the fried food article, and the assessment step includes detecting the extent of deterioration of the oil and fat in accordance with correlation data stored in a memory, the correlation data indicating a correlation between the acoustic data and the extent of deterioration of the oil and fat for each type of the fried food article being handled.

5. A method for controlling a fryer, system comprising:

controlling valves provided to the oil vat of the fryer, via a valve control unit with which said fryer is equipped, based on notification information relating to the extent of deterioration of the oil and fat as outputted by performing the deterioration prediction method according to claim 4; and discharging automatically the oil and fat accommodated in the oil vat as waste oil.

6. The method for controlling the fryer according to claim 5, wherein the valve control unit has further a function that automatically supplies new oil to the oil vat.

7. An oil and fat replacement method such that, based on notification information relating to the extent of deterioration of the oil and fat as outputted by performing the deterioration prediction method according to claim 4, one or more operations are performed, the operations being selected from among:

a) alerting an oil and fat vendor and ordering new oil and fat;

b) alerting an oil and fat manufacturer and producing a plan for manufacturing or selling the oil and fat;

c) alerting a general headquarters of shops or factories, or alerting an oil and fat manufacturer, and issuing a proposal or an instruction regarding the method of use of the oil and fat to the shops or factories being supervised;

d) alerting a waste oil collector or an oil and fat manufacturer and making preparations to collect waste oil; and e) alerting a cleaning work provider and making preparations to clean the oil vat.

* * * * *